(12) United States Patent
Spallek et al.

(10) Patent No.: US 7,819,342 B2
(45) Date of Patent: Oct. 26, 2010

(54) ATOMIZER FOR DISPENSING LIQUIDS FOR MEDICAL PURPOSES

(75) Inventors: Michael Spallek, Ingelheim (DE); Andree Jung, Idar-Oberstein (DE)

(73) Assignee: Boehringer Ingelheim International GmbH, Ingelheim am Rhein (DE)

(*) Notice: Subject to any disclaimer, the term of this patent is extended or adjusted under 35 U.S.C. 154(b) by 734 days.

(21) Appl. No.: 11/120,404

(22) Filed: May 3, 2005

(65) Prior Publication Data
US 2005/0263618 A1 Dec. 1, 2005

(30) Foreign Application Priority Data
May 3, 2004 (DE) .................. 10 2004 021 789

(51) Int. Cl.
| A62C 13/62 | (2006.01) |
| B05B 9/04 | (2006.01) |
| B05B 7/12 | (2006.01) |
| B05B 7/06 | (2006.01) |
| B67D 7/70 | (2010.01) |
| B67D 7/84 | (2010.01) |
| A61M 5/00 | (2006.01) |

(52) U.S. Cl. .................. 239/424.5; 239/304; 239/332; 239/333; 239/409; 239/417.5; 239/427; 239/433; 222/137; 222/162; 604/191

(58) Field of Classification Search .................. 222/129, 222/135, 136, 137, 145.1, 145.5, 162; 239/398, 239/407, 408, 409, 410, 417.5, 418, 433, 239/304, 310, 419, 424.5, 426, 427, 429, 239/434, 332, 333; 604/191
See application file for complete search history.

(56) References Cited

U.S. PATENT DOCUMENTS 4,623,337 A * 11/1986 Maurice .................. 604/298
4,826,048 A * 5/1989 Skorka et al. .................. 222/137
5,289,948 A 3/1994 Moss et al.
5,339,990 A 8/1994 Wilder
5,472,143 A * 12/1995 Bartels et al. .................. 239/462

(Continued)

FOREIGN PATENT DOCUMENTS

| EP | 0520571 | 12/1992 |
| EP | 0918570 | 6/1999 |
| WO | 91/14468 | 10/1991 |
| WO | 9407607 | 4/1994 |
| WO | 97/12687 | 4/1997 |

(Continued)

OTHER PUBLICATIONS

International Search Report for PCT/EP2005/004792 mailed Aug. 4, 2005.

*Primary Examiner*—Dinh Q Nguyen
*Assistant Examiner*—Ryan Reis
(74) *Attorney, Agent, or Firm*—Michael P. Morris; Mary-Ellen M. Devlin; David L. Kershner (57) ABSTRACT

Atomizers (1) comprising a cartridge holder (4) which is arranged in the housing (3), a mouthpiece (5) which is provided on the housing (3) and in which an atomization device (6) is arranged, and a connecting tube system (7) which connects the atomization device (6) and the cartridge holder (4), wherein the atomization device (6) has at least one nozzle body (8) and the connecting tube system (7) has at least one passage (9) with a hollow plunger (10) mounted displaceably therein, wherein the hollow plunger (10) includes a valve body (21). In accordance with a first embodiment the atomizer (1) has a first hollow plunger (10a) mounted displaceably in a first passage (9a) and a second hollow plunger (10b) mounted displaceably in a second passage (9b), wherein the first hollow plunger (10a) and the second hollow plunger (10b) extend into the cartridge holder (4).

19 Claims, 6 Drawing Sheets

U.S. PATENT DOCUMENTS

| | | |
|---|---|---|
| 5,497,944 A | 3/1996 | Weston |
| 5,964,416 A * | 10/1999 | Jaeger et al. ............... 239/333 |
| 6,109,479 A | 8/2000 | Ruckdeschel |
| 6,846,413 B1 | 1/2005 | Kadel |
| 2002/0129812 A1 | 9/2002 | Litherland et al. |
| 2002/0148904 A1* | 10/2002 | Yu ............................. 239/69 |
| 2005/0247312 A1 | 11/2005 | Davies |
| 2005/0251289 A1 | 11/2005 | Bonney et al. |
| 2005/0268908 A1 | 12/2005 | Bonney et al. |
| 2005/0268909 A1 | 12/2005 | Bonney et al. |
| 2005/0274378 A1 | 12/2005 | Bonney et al. |

FOREIGN PATENT DOCUMENTS

| | | | |
|---|---|---|---|
| WO | WO 97/12687 | * | 4/1997 |
| WO | 9916530 | | 4/1999 |
| WO | 2004011067 | | 2/2004 |
| WO | 2004011068 | | 2/2004 |
| WO | 2004011070 | | 2/2004 |
| WO | 2004011071 | | 2/2004 |

* cited by examiner

ATOMIZER FOR DISPENSING LIQUIDS FOR MEDICAL PURPOSES

BACKGROUND OF THE INVENTION

1. Field of the Invention

The invention concerns an atomizer for dispensing liquids for medical purposes, for example pharmaceutical active substance formulations, from at least one container for the liquid, which can be fitted into the atomizer (cartridge), as well as a cartridge and a system comprising an atomizer and a cartridge which can be fitted therein.

2. Description of the Prior Art

The known atomizers include as essential units a cartridge holder which is arranged in the housing, a mouthpiece which is provided on the housing and in which an atomization device is arranged, and a connecting tube system which connects the atomization device and the cartridge holder, wherein the atomization device has at least one nozzle body and the connecting tube system has at least one passage with a hollow plunger mounted displaceably therein, wherein the hollow plunger includes a valve body.

The hollow plungers which are inserted in the atomizers include a valve body. Upon a downward movement of the hollow plunger, in an open position, the valve body permits an intake flow of the formulation or formulations which are already mixed, into the portion of the passage which is downstream of the hollow plunger in the flow direction. Upon an upward movement of the hollow plunger the valve body closes the hollow plunger and, upon further upward movement, the formulation or the mixture disposed downstream of the hollow plunger in the flow direction is compressed to the desired pressure.

Atomizers of that kind are used for the application of liquid drug formulations which are effective by inhalation, in which case the liquid formulations must satisfy high quality standards. In order to achieve a good distribution of the active substances in the lung, application of a liquid formulation which does not involve the use of propellant gases, by means of inhalers or atomizers which are suitable for that purpose, presents itself as an option. Particularly suitable atomizers are those which can nebulize a small amount of a liquid formulation in the therapeutically necessary dosage into a therapeutically-inhalatively suitable aerosol, within a few seconds. In that respect the nebulization duration should be optimized in respect of time in order to guarantee optimum lung deposition. In accordance with the present invention, those nebulizers are preferred, in which an amount of less than 100 microliters, preferably less than 50 microliters, quite preferably less than 20 microliters of active substance solution are already atomized with one stroke or a few strokes to afford an aerosol with an average particle size of less than 20 micrometers, preferably less than 10 micrometers.

Such a device for propellant gas-free administration of a dosed amount of a liquid drug for inhalation use is described in detail for example in international patent application WO 91/14468 'Atomizing Device and Methods' and also in WO 97/12687. In such an atomizer a drug solution is converted by means of high pressure of up to 500 bars into a lung-treating aerosol.

In the known atomizers the active substance formulations are stored in the form of solutions in a reservoir. In that case it is necessary for those solutions used to enjoy adequate storage stability and at the same time to be such that they can be applied directly in accordance with the medical purpose as far as possible without further manipulation. In addition, they should not have any constituents that can interact with the atomizer, so that neither the atomizer, nor the solution, nor the aerosol produced, suffer damage.

Nebulization of the solution is effected by using a special nozzle as is described for example in WO 94/07607 or WO 99/16530.

A further development in the construction of the preferred inhaler is also disclosed in WO 97/12687.

By virtue of its cylinder-like shape and its easily manageable size of less than 9 to 15 cm in length and 2 to 4 cm in width the known atomizers can be carried around by the patient at any time. The atomizer sprays a defined volume of the drug formulation using high pressures through small nozzles so that inhalable aerosols are produced.

EP 0 918 570 describes an atomizer for nasal sprays which as core components includes a spring-operated plunger and a nozzle device. It is possible to insert between the plunger and the nozzle a container which at its bottom has a ram and at its head side is closed by way of a seal. That seal of the container is opened prior to the first use by moving the external nozzle which is integrated in the atomizer through the seal.

The described atomizers, however, are primarily suited for the delivery of stable solution formulations, that is to say, for formulation constituents that can be stably mixed with each other and that can be stored over a prolonged period of time. Thus it is a prerequisite for example in the case of combination preparations which contain at least two active substances that the active substances to be administered are for example stable at the same pH-value in the same solvent.

In addition various principles of devices for administering medicaments are known from the state of the art, which are stored separately prior to their administration but which are then available to the patient as a mixture.

WO2004/011068 discloses an electronic system for the administration of medicament mixtures.

WO2004/011071 discloses a system for administering medicaments, wherein the two medicament containers are of different kinds.

WO2004/011067 and 011070 also disclose systems for administering medicament mixtures, wherein 01170 claims the administration of a plurality of co-formulated medicaments with a medicament which is not suitable for co-formulation.

WO2004/011067 claims a simple system for administering medicaments which are stored in separate containers but which can be administered to the patient in the form of a mixture.

SUMMARY OF THE INVENTION

The object of the present invention is now that of providing an atomizer which also makes it possible to store, mix, and administer formulations, in a flow direction, which can be stably stored only under comparatively different conditions such as for example pH-value, solvent, or additives.

The invention further seeks to provide a cartridge for the storage of the formulations.

A further sub-object of the invention lies in the provision of a system comprising an atomizer and a cartridge.

According to the invention, that object is first attained with an atomizer in which a first hollow plunger is mounted displaceably in a first passage and a second hollow plunger is mounted displaceably in a second passage, wherein the first hollow plunger and the second hollow plunger extend into the cartridge holder. The term hollow plunger is used to denote a tubular plunger whose outside diameter is of only slightly smaller dimension than the inside diameter of the passage. The first and second passages are preferably bores of a round shape in cross-section and which extend in substantially mutually parallel relationship. In that case the passages perform two tasks. On the one hand they serve as a guide for the hollow plunger mounted therein, in the axial direction of movement, while on the other hand the formulation of the active substance is passed through therein on the way to the nozzle body. The portion of the passage from the nozzle body to the end of the hollow plunger, which is downstream in the flow direction, at the same time represents a pressure chamber whose volume progressively decreases upon an upward movement of the hollow plunger. The front end of the hollow plunger, which is in the flow-direction, projects into the cartridge holder.

Advantageously, the atomization device includes a first nozzle body with at least one first nozzle outlet and a second nozzle body with at least one second nozzle outlet, wherein the first nozzle body is connected to the first passage and the second nozzle body is connected to the second passage. In this embodiment two different liquids are passed completely separately from each other through the atomizer and are only combined to form an aerosol cloud outside the device. As a result of this contacts between different formulations and reactions resulting therefrom during storage and atomization are minimized.

The first nozzle outlet of the first nozzle body and the second nozzle outlet of the second nozzle body can be inclined relative to each other so that the two liquids meet and experience mutual atomization outside the atomizer.

It has proven to be particularly desirable if the first nozzle body has two nozzle outlets and the second nozzle body has two nozzle outlets, wherein the two nozzle outlets of a nozzle body are preferably inclined relative to each other. In that case two liquids are atomized in parallel relationship in respect of time, so that two aerosol clouds are produced which mutually interpenetrate. In principle, instead of two separate nozzle outlets per nozzle head, still further nozzle outlets are possible.

In accordance with another embodiment the atomization device has only one nozzle body, wherein the first and second passages are guided into the nozzle body and are each provided with a first and a second nozzle outlet. In that case a common aerosol cloud is formed from the two issuing liquid jets after issue thereof from separate nozzle outlets. In this embodiment also the first nozzle outlet and the second nozzle outlet of the common nozzle body are inclined relative to each other so that the two liquid jets meet in front of the nozzle body, thereby providing for mutual atomization.

In addition, a plurality of separate nozzle bodies which each have two or more nozzle outlets make it possible for different particle sizes to be simultaneously produced from the different formulations. Thus for example a larger particle size of a first formulation can be administered for treatment of the upper airways and at the same time a smaller lung-reaching particle size of the second formulation can be administered for treatment of the lower airways.

In a further advantageous embodiment the atomization device includes a nozzle body, in front of which in the flow direction is arranged a mixing passage in which the first and second passages are brought together. That mixing passage feeds the solution which has already been mixed to the nozzle body. Preferably in this embodiment also there are two nozzle outlets which are inclined relative to each other and with which an aerosol cloud is produced.

As an alternative to the above-described embodiment the atomization device can also have a nozzle body with a plenum chamber which is arranged therein and in which the first and second passages are brought together. In this embodiment the mixing passage has been moved into the nozzle body and is referred to as a plenum chamber in order to distinguish it from the foregoing embodiment. Production of the aerosol cloud is implemented in a manner corresponding to the above-described embodiments.

The object of the invention is also attained with an atomizer in which at least one of the hollow plungers is branched at its end near the cartridge holder into a first and a second plunger portion, wherein the first and the second plunger portions extend into the cartridge holder. In that configuration a hollow plunger is mounted displaceably in a passage. Outside the passage the hollow plunger branches into two plunger portions. As a departure from the above-described embodiments, preparation of the mixture consisting of two formulations does not take place in the mixing or plenum chamber but already occurs in the hollow plunger. For producing the aerosol cloud, this atomizer can also have in the single nozzle body a first and a second nozzle outlet which are preferably respectively inclined relative to each other.

In all embodiments, in the case of a plurality of nozzle outlets, the inclined nozzle outlets are oriented in such a way that they produce jet directions of the liquids at an impingement angle of preferably 20° to 160°, particularly preferably 60° to 150° and quite particularly preferably 80° to 100°. The impingement angle crucially determines the impaction spacing, that is to say the spacing from the nozzle outlets at which the two liquids meet. That impaction spacing may not be selected to be too large as otherwise adequate atomization does not take place.

Preferably the nozzle outlets on a nozzle body are arranged at a distance of 10 μm to 200 μm, preferably from 10 μm to 100 μm, particularly preferably 30 μm to 70 μm, most preferably at 50 μm.

Preferably the valve body is arranged at the end of the hollow plunger, which is the downstream end in the flow direction. That prevents a back-flow of the formulation or the mixed formulations into the hollow plunger.

Desirably the at least one nozzle body is fixed stationarily to the at least one passage.

Preferably the cartridge holder is mounted movably.

A stressing element can be arranged in the housing to store a predetermined amount of energy. The stressing element used can be for example a coil spring which can be stressed in its axial direction. Upon actuation of a release button the prestressed stressing element provides the amount of energy and displaces the cartridge holder in the axial direction of the housing, that is to say, in the direction of the atomization device. The properties of the stressing element determine the amount of energy which can be applied to the formulations and thus substantially the attainable fluid pressure of the formulations. The fluid pressure involved is 100 bars to 700 bars, preferably 200 bars to 500 bars.

The first sub-object of the invention is attained by a cartridge which has a first and a second cartridge chamber wherein a first liquid is stored in a first cartridge chamber and a second liquid is stored in a second cartridge chamber which is spatially separated from the first cartridge chamber. In this case the two liquids are disposed in one cartridge, whereby manageability when inserting the cartridge is simplified.

Preferably the cartridge has a peripheral, cover, and bottom wall which is stable in respect of shape.

The further sub-object is attained by a system in which a first liquid is stored in a first cartridge or cartridge chamber and a second liquid is stored in a second cartridge or cartridge chamber which is spatially separated from the first cartridge or cartridge chamber, and a first hollow plunger can be inserted into the first cartridge or cartridge chamber and a second hollow plunger can be inserted into the second cartridge or a first plunger portion connected to the hollow plunger can be inserted into the first cartridge or first cartridge chamber and a second plunger portion can be inserted into the second cartridge or second cartridge chamber.

BRIEF DESCRIPTION OF THE DRAWINGS

For better understanding the invention is described in greater detail hereinafter with reference to the Figures in which.

DESCRIPTION OF THE INVENTION

Hereinafter identical parts are denoted by the same references.

Figure 1:
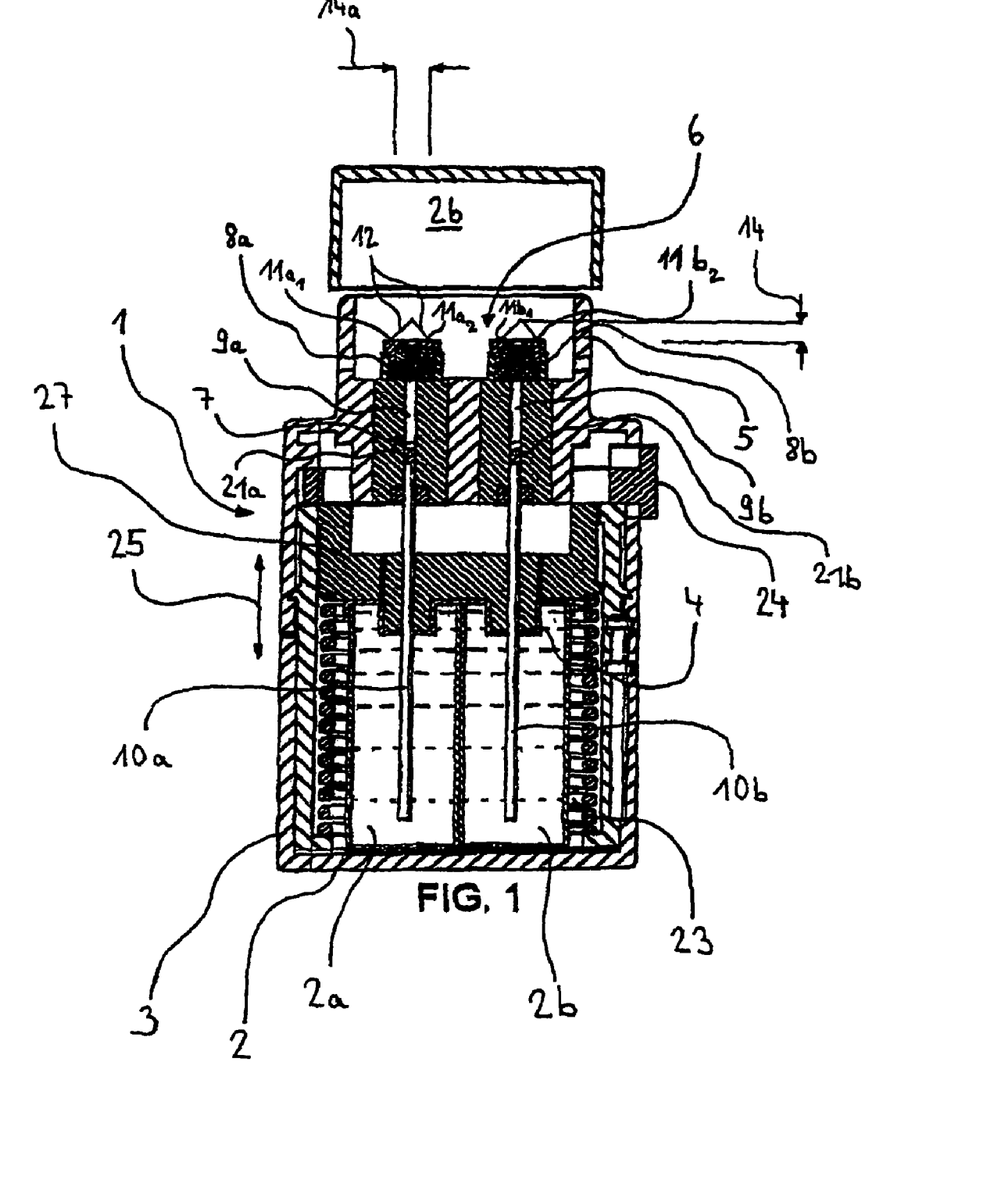
FIG. 1 shows a view in longitudinal section through the atomizer with two nozzle bodies and two passages extending in parallel relationship with hollow plungers guided therein in accordance with a first embodiment with two cartridge chambers in a cartridge.

FIG. 1 shows a view in longitudinal section through the atomizer 1 having a first nozzle body 8*a* and a second nozzle body 8*b* and two passages 9*a*, 9*b* extending in parallel relationship, with hollow plungers 10*a*, 10*b* guided therein, in accordance with a first embodiment. The passages 9*a*, 9*b* and the hollow plungers 10*a*, 10*b* together form the connecting tube system 7.

Figure 2:
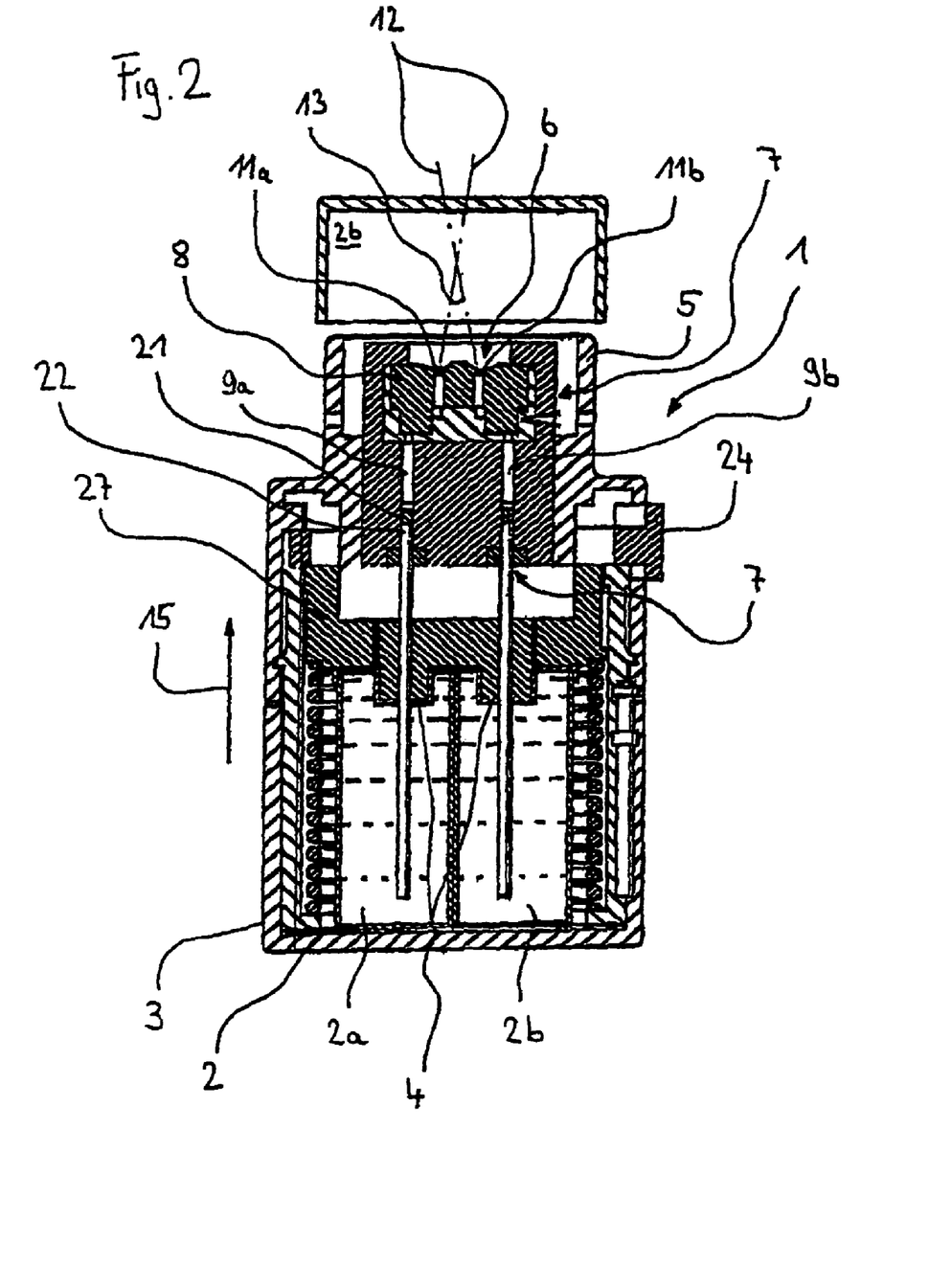
FIG. 2 is a view corresponding to FIG. 1 with a nozzle body and two passages extending in parallel relationship with hollow plungers guided therein in accordance with a second embodiment.

The atomizer includes a housing which is divided into two and which is rotatable relative to each other and by way of which a stressing element 23 can be stressed. Upon actuation of a release button 24 a cup-shaped thrust plate 27 is released and advanced by the spring force of the stressing element 23 in the flow direction 15 (see FIG. 2). In that case the two hollow plungers 10*a*, 10*b* which are fixed to the thrust plate 27 and passed therethrough are also advanced, together with the thrust plate 27, and in so doing compress the liquids which were previously sucked into the passages 9*a*, 9*b* and which then issue from the first nozzle body 8*a* and the second nozzle body 8*b*. The formation of two separate aerosol clouds is effected by way of respective nozzle outlets 11*a*1, 11*a*2, 11*b*1, 11*b*2 arranged in the nozzle bodies 8*a*, 8*b*, that is to say a total of four nozzle outlets.

For renewed use the stressing element 23 is tensioned again, whereby the thrust plate 27 and the hollow plungers 10*a*, 10*b* are displaced with a downward movement. Due to the downward movement of the hollow plungers 10*a*, 10*b*, the respective formulation is sucked out of the cartridge chambers 2*a*, 2*b* into the respective first passage 9*a* or the second passage 9*b*. In that downward movement the two valve bodies 21*a*, 21*b* are in a flow-transmitting position.

Upon actuation of the release button 24 the hollow plungers 10*a*, 10*b* are displaced in the axial direction 25 of the housing 3, that is to say they are displaced with an upward movement. In that case the respective valve body 21*a*, 21*b* automatically closes off the first hollow plunger 10*a* or the second hollow plunger 10*b* and thereby permits the liquid to be compressed. The valve bodies 21*a*, 21*b* are disposed at the rear ends 22 (see FIG. 2) of the respective hollow plunger 10*a*, 10*b*.

Figure 3:
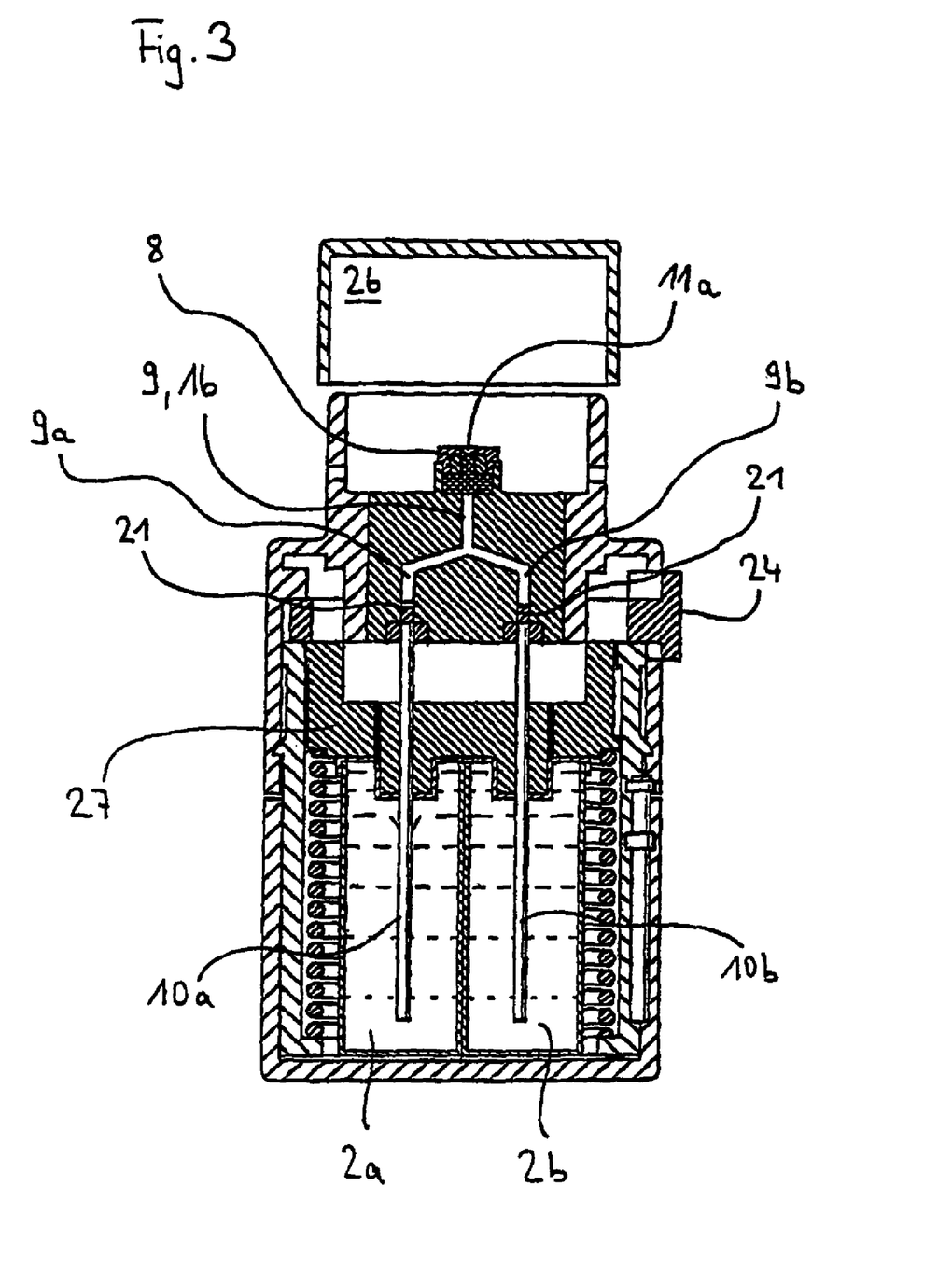
FIG. 3 is a view corresponding to FIG. 1 with a nozzle body and a mixing passage in which the first and second passages are brought together in accordance with a third embodiment.
Figure 4:
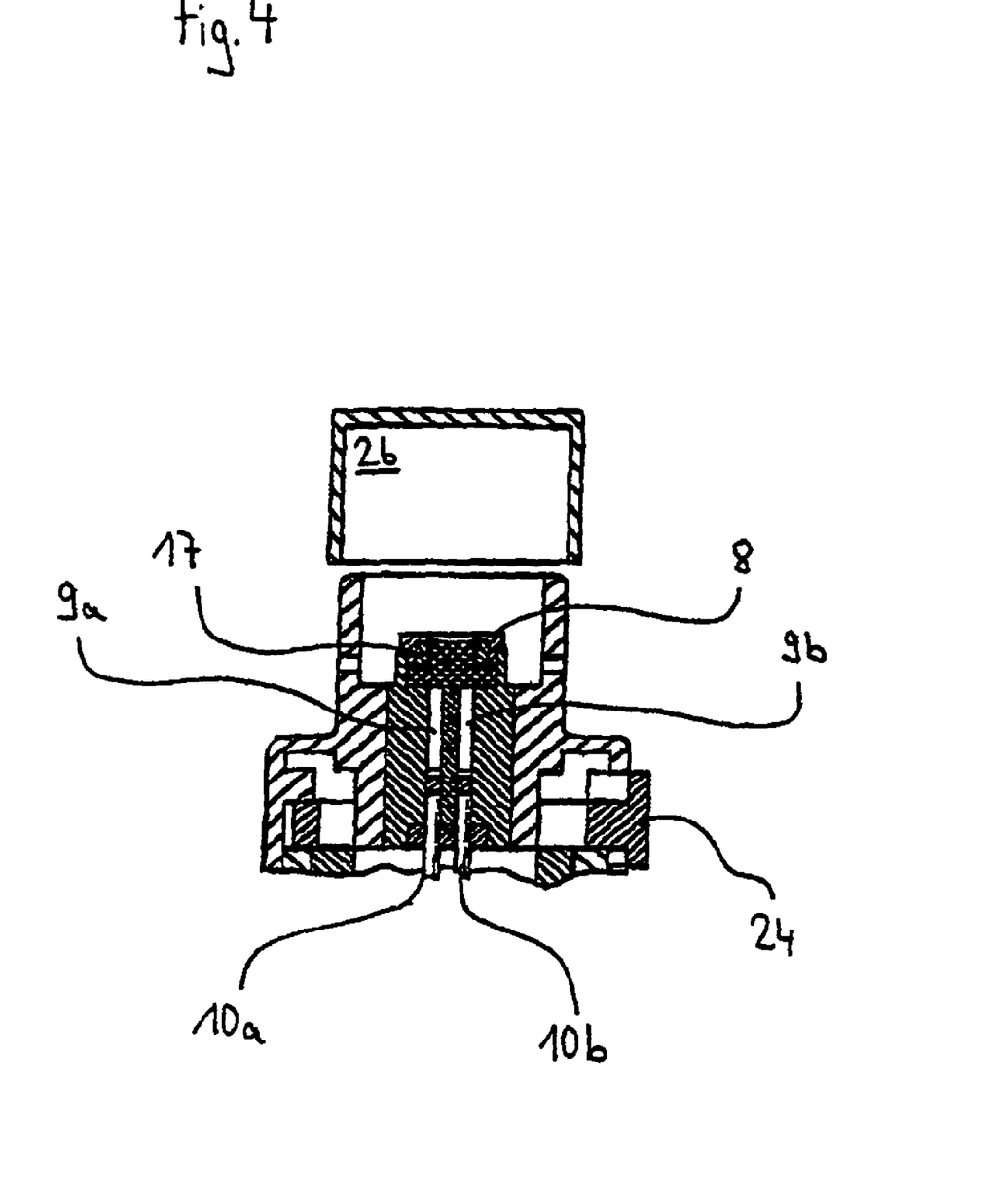
FIG. 4 is a partial view corresponding to FIG. 1 with a nozzle body and a plenum chamber arranged therein, in which the first and second passages are brought together in accordance with a fourth embodiment.

During the upward movement of the first hollow plunger 10*a* and the second hollow plunger 10*b* the patient fits his mouth around the mouthpiece 5 provided on the housing 3 and can inhale the aerosol. The mouthpiece 5 can be covered with a closure cover 26.

In the embodiment shown in FIG. 1 the passages 9*a*, 9*b* are each provided with their own respective nozzle bodies 8*a*, 8*b*. For the passage of the respective liquid the nozzle bodies 8*a*, 8*b* have two nozzle outlets 11*a*1, 11*a*2 on the first nozzle body 8*a* and two further nozzle outlets 11*b*1, 11*b*2 on the second nozzle body 8*b*. The nozzle outlets 11*b*1, 11*b*2 of the second nozzle body 8*b* are oriented in such a way that the liquid jets which issue from the nozzle outlets 11*b*1, 11*b*2 in the jet direction 12 meet at the impaction spacing 14. The same applies for the liquid issuing from the first nozzle body 8*a* from the nozzle outlets 11*a*1, 11*a*2. In that way two separate aerosol clouds are produced, which mix with each other.

The nozzle outlets 11*a*1, 11*a*2 of the first nozzle body 8*a*, like the nozzle outlets 11*b*1, 11*b*2 of the second nozzle body 8*b*, are respectively spaced with respect to each other at the distance 14*a*.

FIG. 2 shows a second embodiment of the atomizer in which the passages 9*a*, 9*b*, in the region of the atomization device 6, extend in a common nozzle body 8 and issue there by way of a separate individual first nozzle outlet 11*a* and a second individual nozzle outlet 11*b*.

As can be seen from FIG. 2 the respective liquids issue at a jet direction 12 and meet in front of the atomizer 1. In that situation the liquids come together at the impingement angle 13. Due to the formulations meeting, particularly fine nebulization and mixing of the formulations is achieved, with an aerosol cloud being produced from the two liquids in this embodiment.

FIG. 3 shows a third embodiment of the invention in which the passage 9 is in the form of a mixing passage 16, that is to say the first passage 9*a* and the second passage 9*b* combine in the mixing passage 16. Hollow plungers 10*a*, 10*b* are mounted displaceably in respective ones of the passages 9*a* and 9*b*.

In the embodiment of FIG. 3 mixing of the two liquids already takes place in the suction process, that is to say, upon a downward movement of the two hollow plungers 10*a*, 10*b*.

Upon an upward movement of the two hollow plungers 10*a*, 10*b* the formulation which has been previously respectively sucked in and which is to be found in the passage 9*a*, 9*b* is compressed and expelled in the direction of the nozzle body 8. A nozzle outlet 11*a* is visible in the view shown in FIG. 3. Mixing of the formulation which is sucked in by way of the hollow plunger 10*a* from the first cartridge chamber 2*a* and that which is sucked in by way of the hollow plunger 10*b* from the second cartridge chamber 2*b* is therefore effected in the mixing passage 16 in this embodiment. The valves 21 prevent a back-flow from the mixing passage 16 back into the cartridge chamber.

FIG. 4 shows a fourth embodiment of the invention which has a plenum chamber 17 disposed in the nozzle body 8, instead of the mixing passage 16 which can be seen from FIG. 3. The passages 9*a*, 9*b* terminate in that plenum chamber 17 so that there the formulations are mixed together upon an upward movement of the hollow plungers. As a departure from the embodiment of FIG. 3 mixing does not take place when the liquids are sucked in but when they are discharged.

Figure 5:
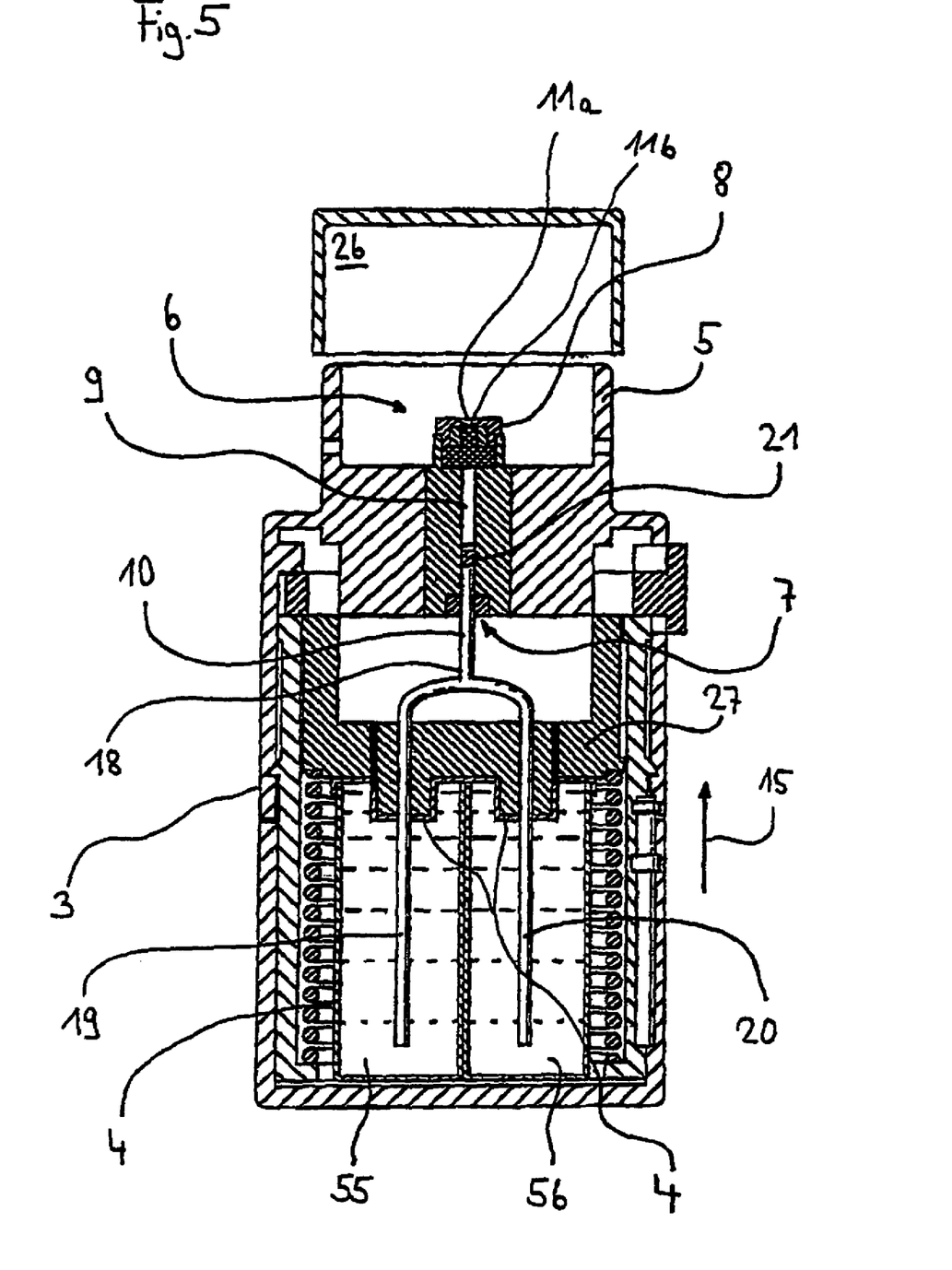
FIG. 5 is a view corresponding to FIG. 1 with a nozzle body and a hollow plunger branched into plunger portions, in accordance with a fifth embodiment.

FIG. 5 shows a further fifth alternative embodiment in which a hollow plunger 10 is mounted displaceably in a passage 9. The single passage 9 terminates in the flow direction 15 in the nozzle body 8 through which the solution mixture can issue by way of the nozzle outlets 11a, 11b. Only the first nozzle outlet 11a is visible in the FIG. 5 view. Outside the plunger 9, in the region of the end 18 of the hollow plunger 10, which is near the cartridge holder, the hollow plunger 10 branches into a first plunger portion 19 and a second plunger portion 20. In this case both plunger portions 19, 20 extend into the cartridge holder 4.

As a departure from the above-illustrated embodiments, two physically separate cartridges are disposed in the cartridge holder 4, namely a first cartridge 55 and a second cartridge 56. This embodiment is less preferred.

Figure 6:
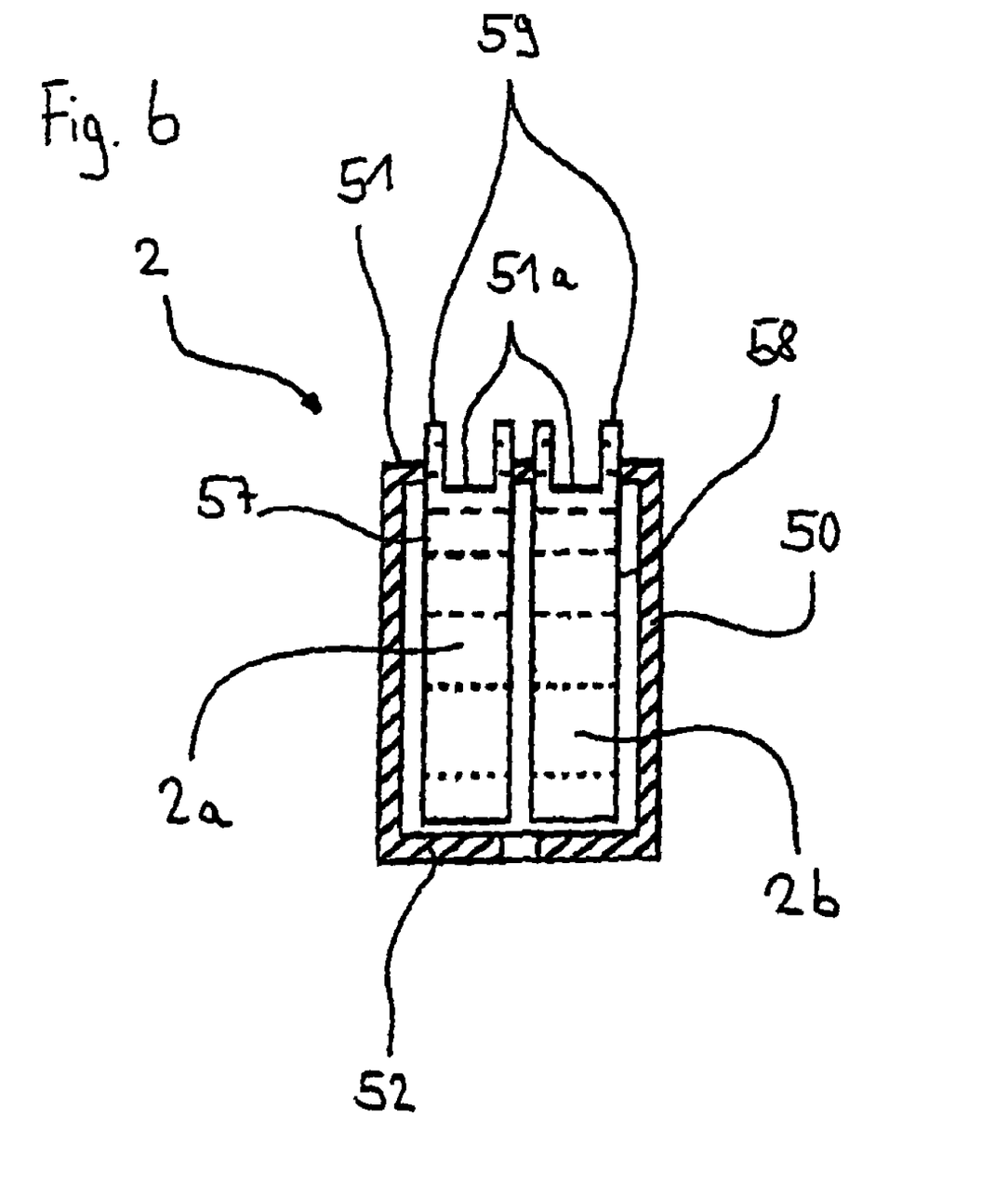
FIG. 6 is a view in longitudinal section through a cartridge with a first and a second cartridge chamber.

FIG. 6 shows a cartridge 2 according to the invention having a cylindrical cartridge chamber 2a and a cartridge chamber 2b which is disposed therebeside and which is also cylindrical.

The two cartridge chambers 2a, 2b have their own internal walls 57, 58 which are arranged in spaced relationship with the peripheral wall 50 and the bottom wall 52. The cover wall 51 is pierced by insertion aids 59 into which the hollow plungers 10a, 10b can engage and, after the closure diaphragm 51a is pierced, can be inserted into the first cartridge chamber 2a and the second cartridge chamber 2b.

LIST OF REFERENCES 1 atomizer
2 cartridge
2a first cartridge chamber
2b second cartridge chamber
3 housing
4 cartridge holder
5 mouthpiece
6 atomization device
7 connecting tube system
8 nozzle body
8a first nozzle body
8b second nozzle body
9 passage
9a first passage
9b second passage
10 hollow plunger
10a a first hollow plunger
10b second hollow plunger
11a first nozzle outlet nozzle body
11b second nozzle outlet nozzle body
11a1 first nozzle outlet first nozzle body
11a2 second nozzle outlet first nozzle body
11b1 first nozzle outlet second nozzle body
11b2 second nozzle outlet second nozzle body
12 jet direction
13 impingement angle
14 impaction spacing
14a distance nozzle outlets of a nozzle body
15 flow direction
16 mixing passage
17 plenum chamber
18 end of the hollow plunger (10) near the cartridge holder
19 first plunger portion
20 second plunger portion
21a first valve body
21b second valve body
22 rear end of hollow plunger
23 stressing element
24 release button
25 axial direction of the housing (3)
26 closure cover
27 thrust plate
50 peripheral wall cartridge
51 cover wall cartridge
51a closure diaphragm
52 bottom wall cartridge
55 first cartridge
56 second cartridge
57 internal wall first cartridge
58 internal wall second cartridge
59 insertion aids

We claim:

1. An atomizer for mixing and dispensing a liquid for medical purposes, comprising:
   a cartridge holder, operable to receive at least one cartridge therein, which is arranged in the housing,
   a mouthpiece which is provided on the housing and includes an atomization device, which is operable to dispense the liquid in a flow direction, and
   a connecting tube system which connects the atomization device and the cartridge holder, wherein the atomization device has a plurality of nozzle bodies, each of the nozzle bodies having at least two nozzle outlets that are sized and shaped such that each nozzle body produces one or more particles that are different in size from the other one or more particles of the other nozzle bodies, the connecting tube system has at least one passage with a hollow plunger mounted displaceably therein, and the hollow plunger includes a first hollow plunger mounted displaceably in a first passage and a second hollow plunger mounted displaceably in a second passage,
   wherein the first hollow plunger and the second hollow plunger extend from the at least one cartridge in the flow direction, a first liquid flows from the at least one cartridge through the first hollow plunger in the flow direction, a second liquid flows from the at least one cartridge through the second hollow plunger in the flow direction, and the nozzle outlets of each of the nozzle bodies are spaced and inclined such that the first liquid emerging from the nozzle outlets of the first nozzle body mixes with the second liquid from adjacent nozzle outlets of the second nozzle body in the flow direction to produce the liquid, in a manner that the liquid is atomized to include the one or more differently sized particles by the plurality of nozzle bodies such that the one or more differently sized particles operate to reach and treat different portions of one or more airways of a user of the atomizer.

2. An atomizer according to claim 1, wherein the atomization device includes a first nozzle body with at least one first nozzle outlet and a second nozzle body with at least one second nozzle outlet, wherein the first nozzle body is connected to the first passage and the second nozzle body is connected to the second passage.

3. An atomizer according to claim 2, wherein the first nozzle outlet of the first nozzle body and the second nozzle outlet of the second nozzle body are inclined relative to each other.

4. An atomizer according to claim 2, wherein, wherein the two nozzle outlets of a nozzle body are inclined relative to each other.

5. An atomizer according to claim 1, wherein the first and second passages are guided into at least one of the plurality of nozzle bodies of the atomization device and are each provided with a first and a second nozzle outlet.

6. An atomizer according to claim 1, wherein a mixing passage is arranged in front of at least one of the plurality of nozzle bodies of the atomization device, and the first and second passages are brought together in the mixing passage.

7. An atomizer according to claim 1, wherein at least one of the plurality of nozzle bodies of the atomization device has a plenum chamber which is arranged therein and in which the first and second passages are brought together.

8. An atomizer for mixing and dispensing a liquid for medical purposes, comprising:
   a cartridge holder, operable to receive at least one cartridge therein, which is arranged in the housing,
   a mouthpiece which is provided on the housing and includes an atomization device, which is operable to dispense the liquid in a flow direction, and
   a connecting tube system which connects the atomization device and the cartridge holder, wherein the atomization device has at least two nozzle bodies, each of the nozzle bodies having at least two nozzle outlets that are sized and shaped such that each nozzle body produces one or more particles that are different in size from the other one or more particles of the other nozzle bodies, the connecting tube system has at least one passage with a hollow plunger mounted displaceably therein, and the hollow plunger comprises a first and a second plunger portion such that the first plunger portion is mounted displaceably in a first passage and the second plunger is mounted displaceably in a second passage of the connecting tube system, wherein the first and the second plunger portions extend from the at least one cartridge in the flow direction, a first liquid flows from the at least one cartridge through the first plunger portion in the flow direction, a second liquid flows from the at least one cartridge through the second plunger portion in the flow direction, and the nozzle outlets of each of the nozzle bodies are spaced and inclined such that the first liquid emerging from the nozzle outlets of the first nozzle body mixes with the second liquid from adjacent nozzle outlets of the second nozzle body in a manner that the liquid is atomized to include the one or more differently sized particles by the plurality of nozzle bodies such that the one or more differently sized particles operate to reach and treat different portions of one or more airways of a user of the atomizer.

9. An atomizer according to claim 8, wherein the at least two nozzle outlets of a common nozzle body are inclined relative to each other.

10. An atomizer according to claim 9, wherein the inclined nozzle outlets are oriented in such a way that they produce jet directions of the liquids at an impingement angle selected from the group consisting of: 20° to 160°, 60° to 150°, and 80° to 100°.

11. An atomizer according to claim 10, wherein the nozzle outlets arranged on a nozzle body are arranged at a distance selected from the group consisting of: 10 μm to 200 μm, 10 μm to 100 μm, 30 μm to 70 μm, and at 50 μm.

12. An atomizer according to claim 1, wherein a valve body is arranged at the end of the hollow plunger, which is the downstream end in the flow direction.

13. An atomizer according to claim 1, wherein the at least one nozzle body is fixed stationarily to the at least one passage.

14. An atomizer according to claim 1, wherein the cartridge holder is mounted movably.

15. An atomizer according to claim 1, wherein a stressing element is arranged in the housing to store a predetermined amount of energy.

16. An atomizer according to claim 15, wherein upon actuation of a release button the stressing element provides the amount of energy and displaces the cartridge holder in the axial direction of the housing.

17. An atomizer according to claim 15, wherein the stressing element displaces the cartridge in the direction of the atomization device.

18. A system comprising an atomizer for mixing and dispensing a liquid for medical purposes, comprising:

a cartridge holder, operable to receive at least one cartridge therein, which is arranged in the housing, a mouthpiece which is provided on the housing and includes an atomization device, which is operable to dispense the liquid in a flow direction, and a connecting tube system which connects the atomization device and the cartridge holder, wherein the atomization device has a plurality of nozzle bodies, each of the nozzle bodies having at least two nozzle outlets that are sized and shaped such that each nozzle body produces one or more particles that are different in size from the other one or more particles of the other nozzle bodies, and the connecting tube system has at least one passage with a hollow plunger mounted displaceably therein, wherein a first liquid is stored in a first cartridge or cartridge chamber and a second liquid is stored in a second cartridge or cartridge chamber which is spatially separated from the first cartridge or cartridge chamber, and wherein the nozzle outlets of each of the nozzle bodies are spaced and inclined such that the first liquid emerging from the first and second nozzle outlets of the first nozzle body mixes with the second liquid from the first and second nozzle outlets of the second nozzle body in the flow direction to produce the liquid, and the liquid is atomized into the one or more differently sized particles by the plurality of nozzle bodies such that the one or more differently sized particles operate to reach and treat different portions of one or more airways of a user of the atomizer.

19. An atomizer according to claim 15, wherein the branched end of the hollow plunger is located between the stressing element and the passage of the connection tube system.

* * * * *